(12) United States Patent
Yao et al.

(10) Patent No.: US 8,004,526 B2
(45) Date of Patent: Aug. 23, 2011

(54) WAVEFORM DATA DISPLAY DEVICE AND METHOD

(75) Inventors: Li Yao, Shenzhen (CN); Xuguang Ci, Shenzhen (CN); Hua Tao, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 972 days.

(21) Appl. No.: 11/923,024

(22) Filed: Oct. 24, 2007

(65) Prior Publication Data

US 2009/0002372 A1    Jan. 1, 2009

(30) Foreign Application Priority Data

Jun. 27, 2007    (CN) .......................... 2007 1 0076148

(51) Int. Cl.
*G06T 11/20* (2006.01)
*G09G 5/22* (2006.01)
*A61B 5/00* (2006.01)

(52) U.S. Cl. ...................... 345/440; 345/440.1; 600/301

(58) Field of Classification Search .................. 600/301; 345/440, 440.1

See application file for complete search history.

(56) References Cited

U.S. PATENT DOCUMENTS

| | | | | |
|---|---|---|---|---|
| 5,214,753 A | * | 5/1993 | Lee et al. | 345/610 |
| 5,444,825 A | * | 8/1995 | Bain et al. | 345/443 |
| 5,830,150 A | * | 11/1998 | Palmer et al. | 600/523 |
| 5,953,009 A | * | 9/1999 | Alexander | 715/771 |
| 5,959,607 A | * | 9/1999 | Montijo | 345/440.1 |
| 6,859,205 B1 | * | 2/2005 | Kishi | 345/443 |
| 2002/0060693 A1 | * | 5/2002 | Ito | 345/690 |
| 2005/0104884 A1 | * | 5/2005 | Iwata et al. | 345/440 |
| 2005/0206644 A1 | * | 9/2005 | Kincaid | 345/440 |

(Continued)

FOREIGN PATENT DOCUMENTS

CN    1572238 A    2/2005

(Continued)

OTHER PUBLICATIONS

AI Horizon, "Recursion and Iteration", http://www.aihorizon.com/essays/basiccs/general/recit.html, Dec. 11, 2003.pdf.*

(Continued)

*Primary Examiner* — Daniel Washburn
*Assistant Examiner* — Jeffrey Chow
(74) *Attorney, Agent, or Firm* — Kory D. Christensen; Stoel Rives LLP

(57) ABSTRACT

This invention discloses a waveform data display device and method, wherein the device comprising a microprocessor, for receiving collected parameter information and generating information on a position, a length and a color value with the maximum brightness of each vertical line for drawing a waveform corresponding to the received parameter information; a logic processing apparatus, for calculating the color values gradually changing along the length of the vertical line at different positions of each vertical line based on the generated information on the length and the color value with the maximum brightness of each vertical line, and combining waveform information of the waveform based on a display time sequence, the generated information on the position of each vertical line and the calculated color values gradually changing along the length of the vertical line at different positions of each vertical line; and, a display unit for displaying the waveform based on the combined waveform information. The waveform data display device and method not only improve the display quality of the waveform but also save CPU computation ability and transmission bandwidth.

7 Claims, 4 Drawing Sheets

U.S. PATENT DOCUMENTS

2006/0063981 A1* 3/2006 Sotos et al. ............... 600/301
2007/0229426 A1* 10/2007 You ........................... 345/89
2007/0244954 A1* 10/2007 Belluomini et al. ........ 708/628

FOREIGN PATENT DOCUMENTS

| CN | 1577245 A | 2/2005 |
| CN | 1636673 A | 7/2005 |
| GB | 2 175 725 A | 12/1986 |
| JP | 03068086 A * | 3/1991 |
| JP | 3-116276 | 5/1991 |
| JP | 6-332972 | 12/1994 |
| JP | 7-287721 | 10/1995 |
| JP | 2004-220279 | 8/2004 |

OTHER PUBLICATIONS

Pendleton, Bob, "Doing it Fast", http://www.gameprogrammer.com/4-fixed.html, Mar. 27, 1997.pdf.*

* cited by examiner $$dx = \max|(x_1 - x_0), (y_1 - y_0)|$$
$$dy = \min|(x_1 - x_0), (y_1 - y_0)|$$
$$d = 2 * dy - dx$$
$$incrE = 2 * dy$$
$$incrNE = 2 * (dy - dx)$$
$$x = x_0$$
$$y = y_0$$
$$sx = sign(x_1 - x_0) \times 1$$
$$sy = sign(y_1 - y_0) \times 1$$

End ← no — $dx > 0$ yes yes — $d \leq 0$ — no $$d = d + incrE$$
$$x = x + sx$$

$$d = d + incrNE$$
$$x = x + sx$$
$$y = y + sy$$

$$dx = dx - 1$$

WAVEFORM DATA DISPLAY DEVICE AND METHOD

TECHNICAL FIELD

The invention relates to a waveform display device and method, and particularly relates to a waveform display device and method for a variety of physiological parameters.

BACKGROUND ART

With the development of detecting technology, the display technology for the real-time waveform display of detected parameters is developing continuously. For instance, a medical monitor is a kind of device that can display a variety of physiological parameters promptly and simultaneously. Current medical monitors can display a variety of physiological parameters, such as IBP, NIBP, CO, CO2, SPO2, ECG and the like, while multi-lead ECG parameters require to display multichannel ECG parameters on one screen. The medical monitor will draw waveform data of amplitude of each parameter changing with time, in order to reflect the changing information of these parameters.

Since the parameters will change with time, the parameter data measured at adjacent points are normally different, sometimes significantly different, so that the waveform data displayed on the screen is not changed continuously. Therefore, the difficult point of waveform date display is the problem of how to smoothen the waveform.

Several methods for drawing waveform data on a screen is proposed in order to solve the problem of smoothening a waveform.

The early method is a point-painting method that fills the gaps between incontinuous waveform data with vertical lines when drawing waveform data on screen, to overcome incontinuity of waveforms. The point-painting method is relatively simple, but because vertical lines are used for filling, and when two waveform data points have different horizontal coordinates, the displaying will present much more incontinuous points, so that the smoothening effect of the waveform is very poor and can not satisfy vision demands when using the point-painting method.

In order to overcome the drawbacks of the point-painting method, an interpolation fitting method is then proposed to draw waveform data. Different from the point-painting method, the interpolation fitting method achieve the purpose of waveform smoothing by extending two adjacent waveform data points and interpolating the fitting data therein. However, there are also drawbacks in the interpolation fitting method because this method needs to interpolate as many interpolation data as possible to achieve the purpose of smoothening a waveform, while it needs a large number of multiplication and division operations to produce a large number of interpolation data, and the length of the waveform displayed on one screen will be reduced and thus the information content displayed will be decreased due to a plurality of fitting data interpolated.

Therefore, a color level drawing method is proposed to draw waveforms on a screen. The color level drawing method, which is an improvement of the point-painting method, changes the vertical line in the point-painting method to a gradation line gradually changed from a light color to a dark color, so as to the incontinuous parameter data points seem smooth because vision effect. The color level drawing method can better show smooth waveforms on a screen. This drawing method also requires a large number of multiplication and division operations, although the multiplication and division operation number is smaller than the interpolation simulation method. Moreover, using the color level drawing method, the amount of information transmitted between a CPU and a hardware processing module will be increased due to the subsection of the vertical lines, this proposes a higher requirement for the operation ability of the CPU and transmission bandwidth of the hardware when the number of waveform displayed on one screen increased.

SUMMARY OF THE INVENTION

In view of the above drawbacks, an object of the invention is to provide a waveform data display device and method which use improved waveform color level drawing method for processing the waveform display, so as to both improve the quality of waveform display and reduce the requirement to the operation ability of the CPU and the transmission bandwidth.

Another object of the invention is to provide a waveform data display device and method which use, for vertical lines with different lengths, different methods to calculate the color value gradually changing along the vertical line length at different positions of vertical lines, to further reduce the data amount of calculation and the data amount of transmission.

To achieve the above objects, the invention provides a waveform data display device comprising: a microprocessor, for receiving collected parameter information and generating information on a position, a length and a color value with the maximum brightness of each vertical line for drawing a waveform corresponding to the received parameter information; a logic processing apparatus, for calculating the color values gradually changing along the length of the vertical line at different positions of each vertical line based on the generated information on the length and the color value with the maximum brightness of each vertical line, and combining waveform information of the waveform based on a display time sequence, the generated information on the position of each vertical line and the calculated color values gradually changing along the length of the vertical line at different positions of each vertical line; and, a display unit for displaying the waveform based on the combined waveform information.

To achieve the above said objects, the invention provides a waveform data display method comprising: receiving, by a microprocessor, collected parameter information and generating information on a position, a length and a color value with the maximum brightness of each vertical line for drawing a waveform corresponding to the received parameter information; calculating, in another processing apparatus different from the microprocessor, color values gradually changing along the length of the vertical line at different positions of each vertical line based on the generated information on the length and the color value with the maximum brightness of each vertical line; combining waveform information of the waveform according to a display time sequence, the generated information on the position of each vertical line and the calculated color values gradually changing along the length of the vertical line at different positions of each vertical line; and, displaying the waveform based on the combined waveform information.

BRIEF DESCRIPTION OF THE DRAWINGS

The features and advantages of the invention will be described in detail by the following embodiments in conjunction with the drawings, wherein.

MODE OF CARRYING OUT THE INVENTION

Figure 1:
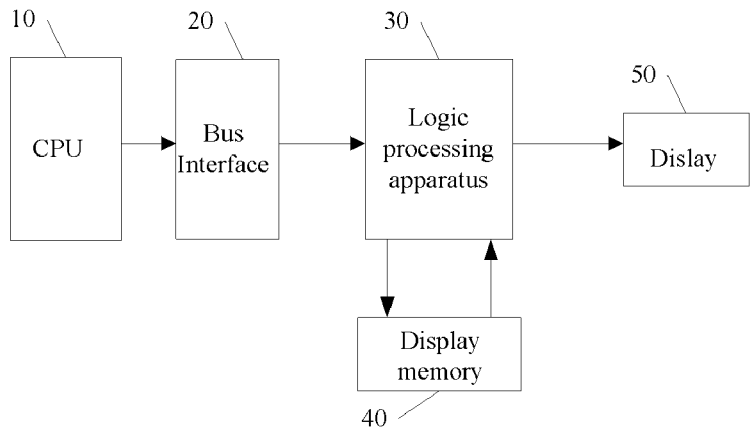
FIG. 1 shows a schematic view of the structure of a waveform data display device according to an embodiment of the invention.

FIG. 1 shows a schematic view of the structure of a waveform data display device according to an embodiment of the invention. As shown in FIG. 1, a waveform data display device 1 comprises a CPU 10, a bus interface 20, a logic processing apparatus 30, a display memory 40 and a display 50. The CPU 10 receives the detected parameter data, generates information on the position and length (start coordinates and length or end coordinates and length of each vertical line) of each vertical line for drawing the waveform corresponding to the received parameter, and its color value with the maximum brightness, and transmits them to the logic processing apparatus 30 via the bus interface 20. After receiving the information on the position and length and the color value with the maximum brightness of each vertical line from CPU 10, the logic processing apparatus 30 calculates the color values gradually changing along the length of the vertical line at different positions of each vertical line based on the received the information on the length and the color value with the maximum brightness of each vertical line, and stores them in the display memory 40, and when the color values gradually changing along the length of the vertical line at different position of all vertical lines are calculated, the waveform information of the parameter data is combined according to a display time sequence, the generated information on the position of each vertical line and the color values gradually changing along the length of the vertical line at different position of each vertical line stored in the display memory 40 and outputted to the display 50. The display 50 displays the waveform of the parameter data on a screen, according to the waveform information from the logic processing apparatus 30.

Figure 7:
FIG. 7 is a schematic view of a color gradation of the color level drawing method according to the present invention.

The color level drawing method, which actually is an improvement of the point-painting method, changes the operation of drawing a straight line between two points into the operation of drawing between two points a set of vertical lines closely adjacent in horizontal direction and staggered in vertical direction to the simulate the straight line between two points, wherein, as shown in FIG. 7, each vertical line gradually changes from a brighter color to a dark color such as gray or black within the line length. Such color gradation on a vertical line is a linear change, i.e. the color value at a specific position of a vertical line is in proportion to the distance of the specific position to the start or end position of the vertical line. Therefore, many vertical lines whose colors gradually changes along the length and which are closely adjacent in horizontal direction compose a smooth parameter data waveform. Compared with the interpolation fitting method, the waveform color level drawing method greatly decrease the amount of mathematic operations performed by the CPU, especially the amount of multiplication and division operations, due to the change from the operation of drawing straight lines to the operation of drawing vertical lines closely adjacent in horizontal direction. However, the existing waveform color level drawing method use a CPU to calculate the color values at different positions of each vertical line, thus the CPU needs to proceed a large amount of data transmissions with hardware processing modules related to peripheral waveform displaying, which will occupy CPU resources and lead to a CPU processing bottleneck.

As shown in FIG. 1, in the waveform data display device of the present invention, the function of calculating the color values gradually changing along the length of the vertical line at different positions of each vertical line is achieved by the logic processing apparatus 30 but not the CPU 10, therefore, the CPU doesn't need to proceed a large amount of data transmissions with the hardware processing modules related to peripheral waveform displaying, which solves the problem of processing bottleneck for the CPU.

However, if the logic processing apparatus 30 also uses the existed method used on the CPU to calculate the color values gradually changing along the length of the vertical line at different positions of each vertical line, the logic processing apparatus 30 commonly realized by FPGA or ASIC will have drawbacks.

To be specific, in the existed color level drawing method, the CPU calculates the color values gradually changing along the length of the vertical line at different positions of each vertical line based on floating-point number operation, and this can ensure the processing precision. However, if the logic processing apparatus 30 is based on floating-point number operation, not only the hardware complexity and time sequence convergence will meet larger difficulty but also in the case that the line lengths of the vertical lines are relative long, the operation precision will be affected by the word length effect caused by the accumulated error, and thus the waveform will appear the phenomena of distortion and burr etc in the case that the difference between adjacent points are relatively high.

The above phenomena can be understood by the following example. It is assumed that the maximum color value is ColorMax=Cm, the length of a vertical line is LinMax=Lm, then, when it's required to draw Cm kind of colors equidistantly within Lm points, the step value of color is Step=Cm/Lm, the color value at the $n^{th}$ point in Lm length beginning from 0 is C(n)=Round(n*Step), wherein, Round(a) is the rounding operation.

If a fixed-point number algorithm with 4 decimal fraction digits is used, the maximum error of this step of division can be calculated by the formula of $\epsilon=\frac{1}{2}^4=0.0625$. Then, the largest rounding error (because of the limits of the word length of a computer, a number with relative more digits is replaced with a relative less digits (normally using round rule) and the error produced by this operation is called a rounding error) Emax=$\epsilon$*256=16, which is obviously unacceptable.

Figure 2:
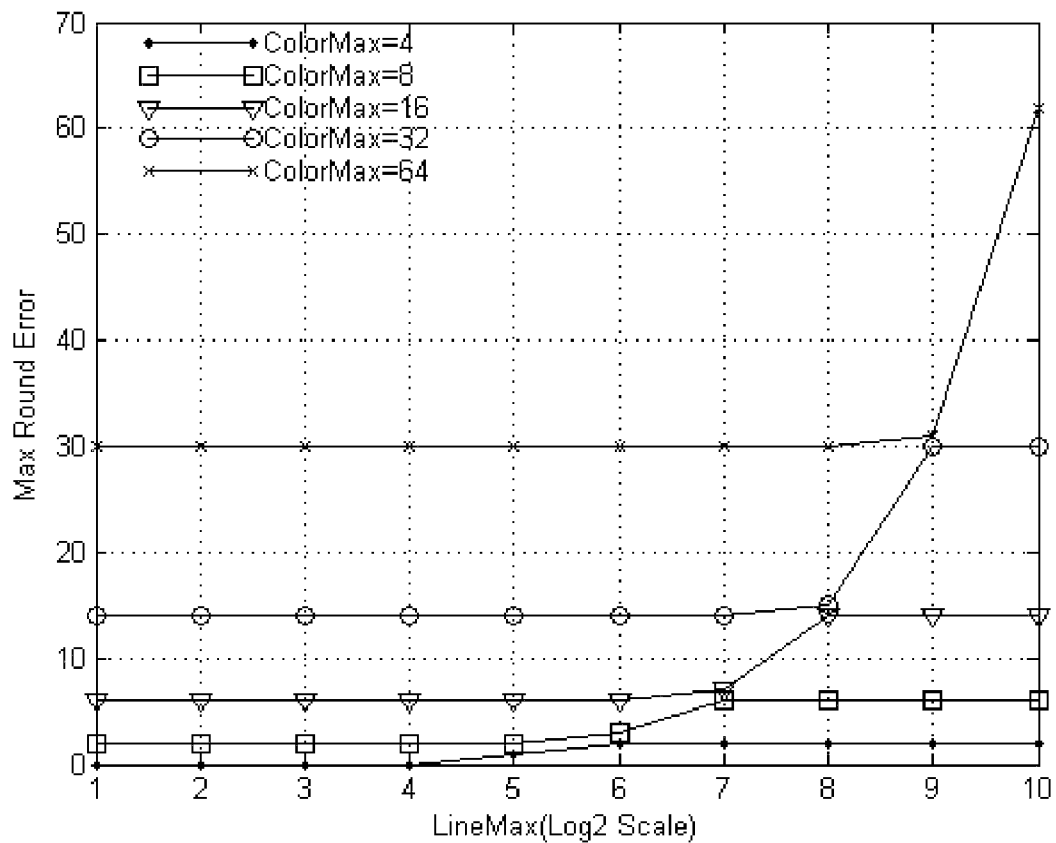
FIG. 2 is a schematic view of the truncation error of the existing color level drawing method.

FIG. 2 shows a schematic view of the maximum error value changed with the length of the vertical line when using the fixed-point number algorithm. In FIG. 2, the word length of the decimal part of a floating-point number is constantly 4, the color value ColorMax with the maximum brightness are 4, 8, . . . , 64 respectively. As can be seen from FIG. 2, the larger the ColorMax is, the larger the error caused by the fixed-point number algorithm is; while given the ColorMax, the error value has the following characteristics: the longer the drawn vertical line is, the larger the error is. At the same time, it can been seed from FIG. 2 that the change trend of such error value has the follow characteristics: when the length of the vertical line is relatively short, the change of the error value is relatively even and fluctuates within a certain range, and there also exists a critical point, before and behind which the error value changes significantly. By analyzing a variety of cases, it can be concluded that the critical point is generally larger than the value of ColorMax, and the critical point is constant when the error precision is given. This characteristic provides a reference for performing optimization to the logic processing apparatus.

To profoundly understand the above problems, the follow discussion is introduced. When the length of the drawn vertical line is 256, in order to keep the rounding error within 0.5 (this range is an acceptable error range), the digits number of the fixed-point decimal is at least $W=\log_2(1/2/256)=9$. If the word length of the integral part is 8, the word length of the entire algorithm performing fixed-point addition will be up to 17 digits. Using such an adder with high digit, it's very difficult to work on high operating frequency even using look ahead carry logic optimization operations. As discussed above, when the length of the waveform straight line is further prolonged, the word length of the fixed-point addition required is increased, therefore, how to solve the problem of contradiction between the fixed-point error and the operation effect appearing in actual operation will become the key problem of using the logic processing apparatus to complete the color level drawing method. At the same time, the characteristic of the error value changing with the length, as shown in FIG. 2, tells us that it's unnecessary to consider the error value of the color level drawing method in the entire range of length, and in the case that the length doesn't exceed ColorMax, the above algorithms can provide good operation precision.

Figure 3:
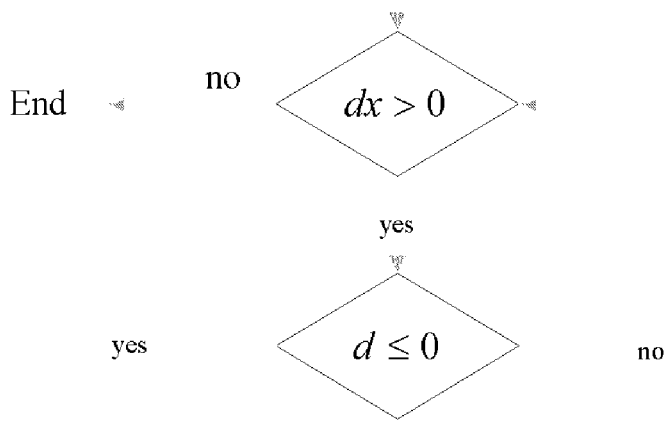
FIG. 3 is a flow chart of the midpoint algorithm.

To solve the above problems, the logic processing apparatus 30 of the invention calculates the color values gradually changing along the length of the vertical line at different positions of each vertical line by introducing the midpoint algorithm in computer graphics. In the field of computer graphics, the Bresenham algorithm as the midpoint algorithm is the most widely used classical straight line scan conversion algorithm only using integers, which uses integral operation when generating straight lines and circle graphics, so as to greatly decrease the amount of calculation and improve the performance effect of the algorithm. FIG. 3 shows a flow chart of the midpoint algorithm in computer graphics, wherein, $(x_0, y_0),(x_1, y_1)$ are the coordinates of two endpoints of the input sloping line, the output $(x, y)$ is the coordinates on the sloping line, the other variables are the intermediate variables for calculation, and $sign(x)$ operation is an operation of extracting the sign. As can be seen for FIG. 3, such midpoint algorithm actually completes the output of sloping line data by iterative operation and by accumulation and error correction, its precision is not depended on the accumulation word length, the entire algorithm is realized by integral operation, and the word length is fixed, in the case that the length is N, only $\log_2(N)$ bits accumulation operations are needed.

In the invention, the logic processing apparatus uses the midpoint algorithm based on integral operation shown in FIG. 3 to calculate the color values gradually changing along the length of the vertical line at different positions of each vertical line. When the midpoint algorithm shown in FIG. 3 is applied to this invention, y1 and y0 represent the length value and the initial value of the vertical line respectively, x1 and x2 represent the color value with the maximum brightness and the initial color value of the vertical line. In the following embodiments of this invention, in order to decrease the amount of operation while considers actual needs, the midpoint algorithm is simplified by setting both y0 and x0 to be zero, so that the color values gradually changing along the length of the vertical line at different positions of each vertical line can be calculated by the logic processing apparatus 30 which only needs the color value Color with the maximum brightness and the total length value Length of each vertical line based on the simplified midpoint algorithm.

THE FIRST EMBODIMENT

Figure 4:
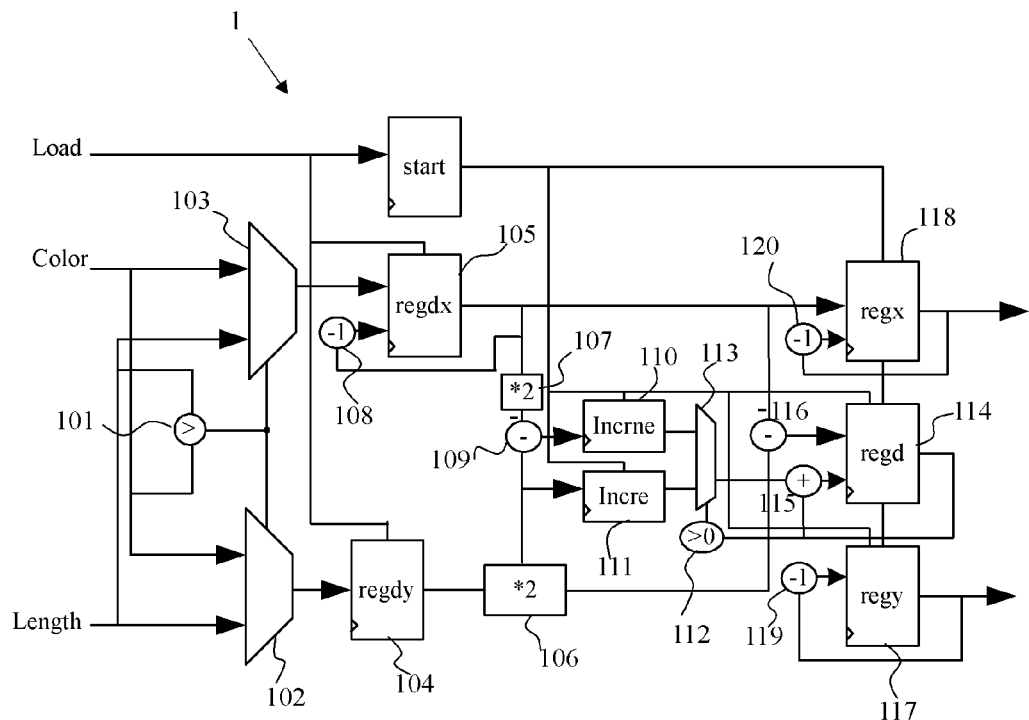
FIG. 4 is a schematic view of the structure of a sloping line midpoint processing unit of a logic processing apparatus according to a first embodiment of the invention.

FIG. 4 is a schematic view of the structure of a sloping line midpoint processing unit of the logic processing apparatus according to the first embodiment of the invention. As shown in FIG. 4, the sloping line midpoint processing unit 1 of the logic processing apparatus 30 comprises a first comparator 101, a first multiplexer 102, a second multiplexer 103, a maximum register 105, a minimum register 104, a first multiplier 106, a second multiplier 107, a fist subtracter 108, a first register 110, a second register 111, a second subtracter 109, a third subtracter 116, a second comparator 112, a third multiplexer 113, a first adder 115, a third register 114, a ninth register 118, a tenth register 117, a second adder 120 and a third adder 119.

The first comparator 101, whose output terminal is coupled to control terminals of the first multiplexer102 and the second multiplexer 103 respectively, receives the length value Length and the color value Color with the maximum brightness of each vertical line; input terminals of the first multiplexer 102, whose output terminal is coupled to the minimum register 104, receives the length value Length and the color value Color with the maximum brightness of each vertical line; an input terminal of the second multiplexer 103, whose output terminal is coupled to the maximum register 105, receives the length value Length and the color value Color with the maximum brightness of each vertical line; the comparison result output from the first comparator 101 is used for controlling the outputs of the first multiplexer102 and the second multiplexer 103, so as to output the larger one between the length value Length and the color value Color with the maximum brightness of each vertical line to the maximum register 105, and to output the smaller one between the length value Length and the color value Color with the maximum brightness of each vertical line to the minimum register 104.

The output terminal of the minimum register 104 is coupled to the first multiplier 106 which performs multiplying 2 to the input values; the output terminal of the maximum register 105 is coupled respectively to the second multiplier 107 which performs multiplying 2 to the input value and the fist subtracter 108 which performs subtracting 1, to perform multiplying 2 operation and subtracting 1 operation respectively; the fist subtracter 108, whose output terminal is coupled to the input terminal of the maximum register 105, subtracts 1 from the value in the maximum register 105, and then output the result to the maximum register 105 to update the value in the maximum register 105, so as to make the value in the maximum register 105 to decrease 1 with the clock each time. The output terminals of the first multiplier 106 and the second multiplier 107 coupled respectively to the input terminals of the second subtracter 109 to perform subtracting the double of the smaller one by the double of the larger one, and the output terminal of the second subtracter 109 is coupled to the input terminal of the first register 110 to store the result of subtracting the double of the smaller one by the double of the larger one into the first register 110; the output terminal of the first multiplier 106 is also coupled to the input terminal of the second register 111 to store the double of the smaller one in the second register 111; the output terminals of the first multiplier 106 and the maximum register 105 are coupled to the third subtracter 116 to realize subtracting the double of the smaller one by the larger one; the output terminal of the third subtracter 116 is coupled to the input terminal of the third register 114 to store the result of subtracting the double of the smaller one by the larger one in the third register 114.

The output terminal of the third register 114 is coupled to the input terminal of the second comparator 112, whose output terminal is coupled to the control terminal of the third multiplexer 113, and which compares the output value of the third register 114 and 0; the output terminals of the first register 110 and the second register 111 are coupled to two input terminals of the third multiplexer 113 whose input terminal is coupled to the input terminal of the first adder 115, the output terminal of the third register 114 also is coupled to the input terminal of the first adder 115 whose output terminal is coupled to the input terminal of the third register 114; the second comparator 112 uses the comparison result between 0 and the value in the third register 114 to control the output of the third multiplexer 113, to make the third multiplexer 113 output the value in the first register 110 when the value in the third register 114 larger than 0, and to make the third multiplexer 113 output the value in the second register 111 when the value in the third register 114 is less than or equal to 0; the sum of the value in the third register 114 and the value output from the third multiplexer 113 is outputted to the third register 114 to update the value in the third register 114.

The output terminal of the ninth register 118 outputs a first calculation value and is coupled to the input terminal of the second adder 120; the output terminal of the second adder 120, whose output terminal is coupled to the input end of the ninth register 118, performs the operation of adding 1 or subtracting 1 to the first calculation value and stores the new step value in the ninth register 118 to update the value in the ninth register 118; the output terminal of the tenth register 117 outputs a second calculation value and is coupled to the input terminal of the third adder 119; the third adder 119, whose output terminal is coupled to the input terminal of the tenth register 117, performs the operation of adding 1 to the first calculation value or subtracting 1 from the first calculation value and stores the new step value in the tenth register 117 to update the value in the tenth register 117; the control terminal of the third register 114 also coupled to the ninth register 118 and the tenth register 117 respectively for outputting control signals to the ninth register 118 and tenth register 117 at each time of updating to control the ninth register 118 to output the fist calculation value, at the same time control the tenth register 117 to output a second calculation value corresponding to the first calculation value, i.e. the third register 114 controls whether the ninth register 118 and the tenth register 117 to carry out stepping, i.e. the third register 114 controls whether the ninth register 118 and the tenth register 117 decrease or stay unchanged. The second adder 120 outputs the first calculation value to the ninth register 118 after adding 1 to it or subtracting 1 from it, to update the value in the ninth register 118; the third adder 119 outputs the second calculation value to the tenth register 117 after adding 1 to it or subtracting 1 from it, to update the value in the tenth register 117. According to cycle calculation by doing this, the ninth register 118 outputs the first calculation value according to the clock, the tenth register 117 outputs the second calculation value according to the clock. If the length value Length and the color value Color with the maximum brightness of each vertical line are input to the ninth register 118 and the tenth register 117 respectively as their initial values, while the second adder 120 and the third adder 119 perform the operation of subtracting 1 respectively, the ninth register 118 outputs the first calculation value as a length value of the decreased vertical line, the tenth register 117 outputs the second calculation value as the decreased color value.

In this embodiment, when the Load signal is caught, the internal start signal will initialize the internal register of the sloping line midpoint processing unit 1. When start signal is effective, the ninth register 118 obtains the value of the maximum register 105 as the initial value. The start signal also inputs initial values to the maximum register 105, the minimum register 104, the first register 110, the second register 111 and the third register 114, and sets the initial value of the tenth register 117 to zero. The Suspend signal not shown in the figure determines the sloping line midpoint processing unit whether to go on working or not.

In this embodiment, according to the practical situation, the step value of the step operation performed by the second adder 120 and the third adder 119 may be other values such as 2 or 3.

THE SECOND EMBODIMENT

Figure 5:
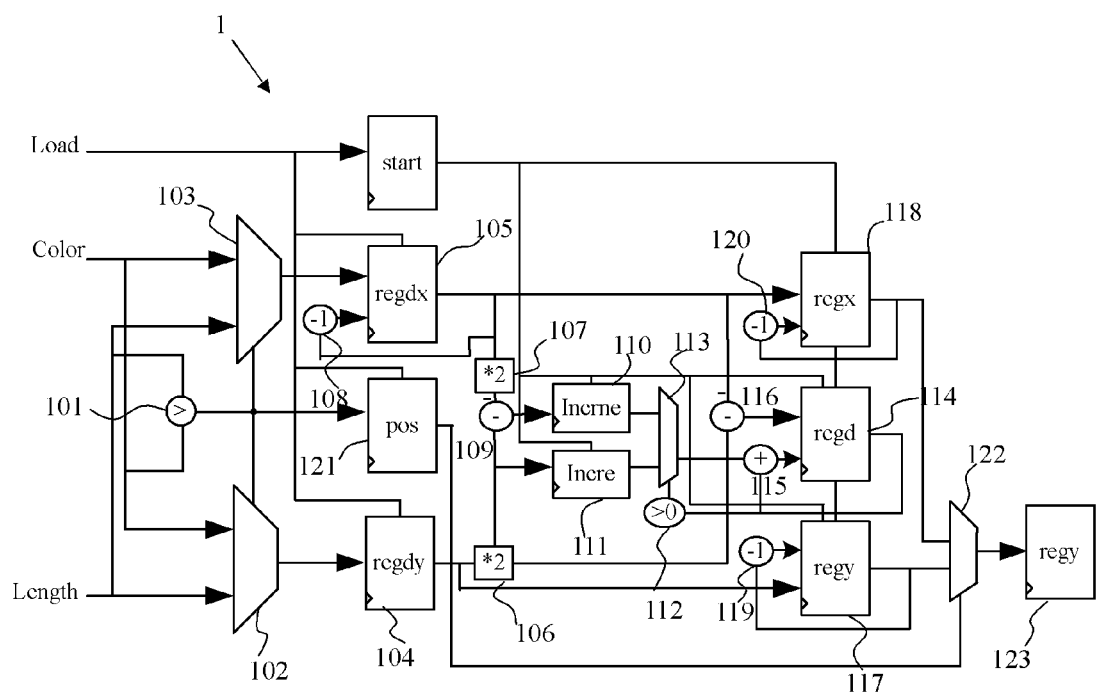
FIG. 5 is a schematic view of the structure of a sloping line midpoint processing unit of a logic processing apparatus according to a second embodiment of the invention.

The difference of the second embodiment from the first embodiment is that an output control is added. FIG. 5 shows a schematic view of the structure of a sloping line midpoint processing unit of the logic processing apparatus according to the second embodiment of the invention. As shown in FIG. 5, compared with the first embodiment, the sloping line midpoint processing unit 1 of the second embodiment also comprises a first comparison result register 121, a fourth multiplexer 122 and a fourth register 123. The second adder 120 outputs the first calculation value to the ninth register 118 after it is subtracted by 1, the third adder 119 outputs the second calculation value to the tenth register 117 after it is subtracted by 1. The output terminal of the first comparator 101 also coupled to the input terminal of the first comparison result register 121 to store the comparison result in the first comparison result register 121 whose output terminal is coupled to the control terminal of the fourth multiplexer 122; the input terminals of the fourth multiplexer 122 receives the first calculation value output from the ninth register 118 and the second calculation value output from the tenth register 117 respectively, and the output terminal of the fourth multiplexer 122 is coupled to the fourth register 123; the output terminal of the maximum register 105 is also coupled to the input terminal of the ninth register 118, for using the larger value between the length value Length and the color value Color with the maximum brightness of each vertical line as the initial value of the ninth register 118; the output terminal of the minimum register 104 is also coupled to the input terminal of the tenth register 117, for using the smaller value between the length value Length and the color value Color with the maximum brightness of each vertical line as the initial value of the tenth register 117; according to the comparison result output from the first comparison result register 121, the fourth multiplexer 122 outputs the second calculation value in the tenth register 117 to the fourth register 123 when the length value Length of the vertical line is larger than or equal to the color value Color with the maximum brightness, and outputs the first calculation value in the ninth register 118 to the fourth register 123 when the length value Length of the vertical line is smaller than the color value Color with the maximum brightness, and the fourth register 123 outputs the value thereof according to the clock.

In this embodiment, when the length value Length of the vertical line is larger than or equal to the color value Color with the maximum brightness, the ninth register 118 outputs the length values of different positions of the vertical line, the tenth register 117 outputs the color values at different positions of the vertical line, and the sloping line midpoint processing unit 1 outputs the values in the tenth register 117 by controlling of the output of the fourth multiplexer 122. When the length value Length of the vertical line is smaller than the color value Color with the maximum brightness, the ninth register 118 outputs the color values at different positions of the vertical line, the tenth register 117 outputs length values of different positions of the vertical line, and the sloping line midpoint processing unit 1 outputs the values in the ninth register 118 by controlling of the output of the fourth multiplexer 122. Thus, the sloping line midpoint processing unit only outputs the color values at different positions of the vertical line under any condition, while the length values of different positions of the vertical line can be obtained by other devices because the length values of different positions of the vertical line are coordinates values decreasing by 1 in unit.

THE THIRD EMBODIMENT

Figure 6:
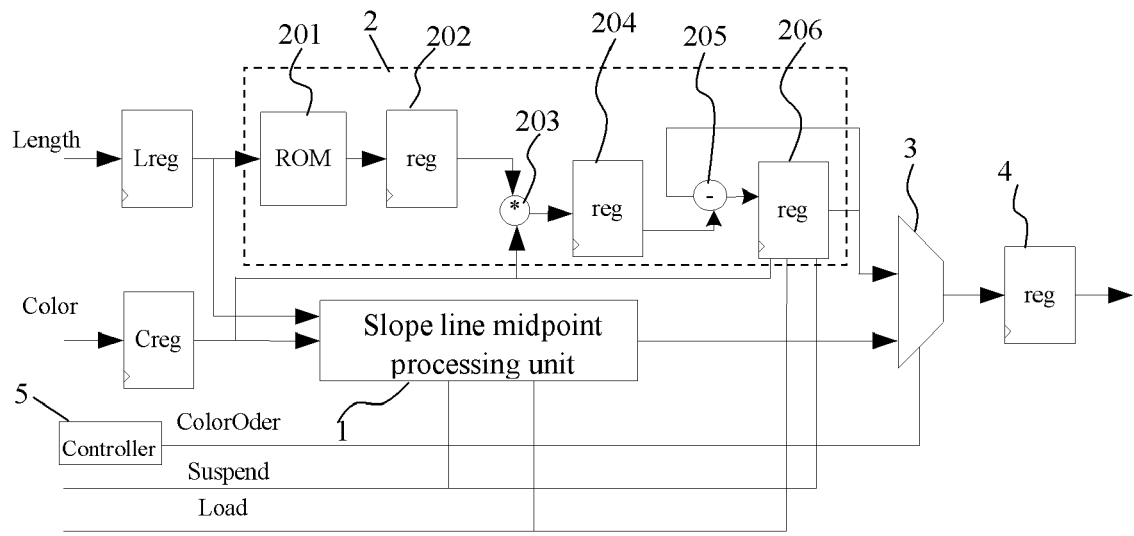
FIG. 6 is a schematic view of the structure of a logic processing apparatus according to a third embodiment of the invention.

It can be known from the above discussion on FIG. 2 that the precision can be guaranteed when using fixed-point number algorithm-based color level drawing method in the case that the length value of the vertical line is relatively small. That is to say, when the length value of the vertical line is smaller than the color value ColorMax with the maximum brightness, the fixed-point number algorithm, which confines the calculation word length in a certain range to guarantee the operation precision when the length value of the vertical line is smaller than the ColorMax, can be used FIG. 6 shows a schematic view of the structure of the logic processing apparatus according to a third embodiment of the invention. As shown in FIG. 6, the logic processing apparatus 30 comprises a sloping line midpoint processing unit 1, a fixed-point number processing unit 2, a controller 5, a fifth multiplexer 3 and a register 4. The output terminal of the sloping line midpoint processing unit 1 and the output terminal of the fixed-point number processing unit 2 are coupled to the input terminal of the fifth multiplexer 3 respectively; the controller 5 outputs control signals to the control terminal of the fifth multiplexer 3 to control the switching of output value of the fifth multiplexer 3 between the value output from the sloping line midpoint processing unit 1 and the value output from the fixed-point number processing unit 2.

Wherein, the solution of the sloping line midpoint processing unit 1 is the same as the above embodiments.

The fixed-point number processing unit 2 receives the length value Length and the color value Color with the maximum brightness of each vertical line and calculates the color values gradually changing along the length of the vertical line at different positions of each vertical line according to fixed-point number algorithm.

The fixed-point number processing unit 2 performs calculation according to the following equation (1)-(3), wherein, the length of the vertical line is Length, the step value is Step, the color value with the maximum brightness is Color, and the color value at a specific position of the vertical line is ColorEx.

$$\text{Step}=\text{Color}/\text{Length}=\text{Color}*(1/\text{Length}) \quad (1)$$

$$\text{ColorEx}=\text{Color} \quad (2)$$

$$\text{If Line}>0 \text{ColorEx}=\text{ColorEx}-\text{Step},\text{Length}=\text{Length}-1 \quad (3)$$

According to the above equation, the fixed-point number processing unit 2 comprises a reciprocal element 201, a third multiplier 203, a fifth register 202, a sixth register 204, a fourth subtracter 205 and a seventh register 206; the reciprocal element 201 receives the length value Length of the vertical line, and outputs the reciprocal of the length value Length of the vertical line to the fifth register 202 whose input terminal is coupled to the input terminal of the third multiplier 203; the third multiplier 203 receives the reciprocal of the length value and the color Color value with the maximum brightness of the vertical line and outputs the product of them to the sixth register 204 whose output terminal is coupled to the input terminal of the fourth subtracter 205; the input terminal of the seventh register 206 receives the color value Color with the maximum brightness, and the output terminal of the seventh register 206 is coupled to the input terminal of the fourth subtracter 205 for outputting the color values; the output terminal of the fourth subtracter 205 is coupled to the seventh register 206 for updating the color value in the seventh register 206.

In the above solution, a division operation for obtaining a reciprocal is first achieved by a ROM reciprocal element 201 (to avoid division operation while the line to be drawn is relatively short and when it's permitted by the internal resources of the logic processing apparatus a lookup table also can be used). Multiplication of the output of the reciprocal element 201 and the input Color is implemented by the third multiplier 203, so as to obtain the step value for performing accumulation, and a new color value can be obtained by subtracting the output color value by the step value Step.

Two registers Lreg and Creg are used respectively to send the output signals to the sloping line midpoint processing unit 1 and the fixed-point number processing unit 2 for perform operation, and the data of which algorithm to be applied as system output is chose by the ColorOder signal output from controller 5.

In the above embodiment, the logic processing apparatus may be implemented with FPGA (field programmable gate array) or ASIC chips or any other logic chips.

It can be seen from the above embodiments that in this invention, the color values gradually changing along the length of the vertical line at different positions of each vertical line for drawing the waveform is calculated by a logic processing apparatus but not a CPU (microprocessor), therefore, not only the display quality of the waveform and promotes the display efficiency of waveform is improved, but also CPU computation ability and transmission bandwidth is saved. Moreover, this invention further simplifies waveform algorithms and guarantees the calculation precision, because it uses different algorithms to calculate the color values gradually changing along the length of the vertical line at different positions for the vertical line whose length is larger than the color value with the maximum brightness and for the vertical line whose length is smaller than the color value with the maximum brightness.

It should be understood by those skilled in this art, the above further descriptions in conjunction with the specific preferred embodiments are used to illustrate the invention, not for confining the invention.

It should be appreciated by those skilled in this art that various changes and modifications may be made to the disclosed waveform data display device without departing from the substance of this invention, therefore, the scope of this invention is defined by the appended claims.

The invention claimed is:

1. A waveform data display device comprising:
 a microprocessor configured to receive collected parameter information and to generate information on a position, a length and a color value with the maximum brightness of each vertical line for drawing a waveform corresponding to the received parameter information;

a logic processing apparatus configured to use the generated information on the length and the color value with the maximum brightness of each vertical line to calculate the color values gradually changing along the length of the vertical line at different positions of each vertical line based on a midpoint algorithm using integer operations, and to combine waveform information of the waveform based on a display time sequence, the generated information on the position of each vertical line and the calculated color values gradually changing along the length of the vertical line at different positions of each vertical line; and a display unit for displaying the waveform based on the combined waveform information, wherein the logic processing apparatus comprises a sloping line midpoint processing unit configured to use the information on the length and the color value with the maximum brightness of each vertical line to calculate the color values gradually changing along the length of the vertical line at different positions of each vertical line based on the midpoint algorithm using integer operations, wherein the sloping line midpoint processing unit (1) comprises: a first comparator (101), a first multiplexer (102), a second multiplexer (103), a maximum register (105), a minimum register (104), a first multiplier (106), a second multiplier (107), a first subtracter (108), a first register (110), a second register (111), a second subtracter (109), a third subtracter (116), a second comparator (112), a third multiplexer (113), a first adder (115), a third register (114), a ninth register (118), a tenth register (117), a second adder (120) and a third adder (119), the first comparator (101), whose output terminal is coupled to control terminals of the first multiplexer (102) and the second multiplexer (103), respectively, receiving the information on the length and the color value with the maximum brightness of each vertical line; the input terminals of the first multiplexer (102) receiving the information on the length and the color value with the maximum brightness of each vertical line, and the output terminal of the first multiplexer is coupled to the minimum register (104) whose output terminal is coupled to the first multiplier (106) for performing multiplying 2 to input values; the input terminal of the second multiplexer (103) receiving the information of the length and the color value with the maximum brightness of each vertical line, and the output terminal of the second multiplexer (103) is coupled to the maximum register (105) whose output terminal is coupled respectively to the second multiplier (107) for performing multiplying 2 to input values and the first subtracter (108) for performing subtracting 1 from the input values; the output terminal of the first subtracter (108) being coupled to the input end of the maximum register (105); the output terminals of the first multiplier (106) and the second multiplier (107) being coupled respectively to the input terminal of the second subtracter (109) whose output terminal is coupled to the input terminal of the first register (110); the output terminal of the first multiplier (106) also being coupled to the input terminal of the second register (111); the output terminals of the first multiplier (106) and the maximum register (105) being coupled to the third subtracter (116) whose output terminal is coupled to the input terminal of the third register (114); the output terminal of the third register (114) being coupled to the input terminal of the second comparator (112), whose output terminal is coupled to the control terminal of the third multiplexer (113), for comparing input values with 0;

the output terminals of the first register (110) and the second register (111) being coupled to two input terminals of the third multiplexer (113) whose input terminal is coupled to the input terminal of the first adder (115), and the output terminal of the third register (114) also being coupled to the input terminal of the first adder (115) whose output terminal is coupled to the input terminal of the third register (114); the output terminal of the ninth register (118) outputting a first calculation value and being coupled to the input terminal of the second adder (120), whose output terminal is coupled to the input terminal of the ninth register (118), for performing addition or subtraction to input values based on a first step value; the output terminal of the tenth register (117) outputting a second calculation value and being coupled to the input terminal of the third adder (119), whose output terminal is coupled to the input terminal of the tenth register (117), for performing addition or subtraction to input values based on a second step value; and the control terminal of the third register (114) also being coupled to the ninth register (118) and the tenth register (117), respectively.

2. The waveform data display device according to claim 1, wherein the first step value and the second step value are 1 or −1.

3. The waveform data display device according to claim 2, wherein the second adder (120) is configured to output the first calculation value to the ninth register (118) after it is subtracted by 1, and the third adder (119) is configured to output the second calculation value to the tenth register (117) after it is subtracted by 1.

4. The waveform data display device according to claim 3, wherein the sloping line midpoint processing unit (1) also comprises a first comparison result register (121), a fourth multiplexer (122) and a fourth register (123);

the output terminal of the first comparator (101) also being coupled to the input terminal of the first comparison result register (121) whose output terminal is coupled to the control terminal of the fourth multiplexer (122) whose input terminal receiving the first calculation value output from the ninth register (118) and the second calculation value output from the tenth register (117) respectively, and the output terminal of the fourth multiplexer (122) being coupled to the fourth register (123);

the output terminal of the maximum register (105) also being coupled to the input terminal of the ninth register (118), for using a larger value between the length and the color value with the maximum brightness of each vertical line as an initial value of the ninth register;

the output terminal of the minimum register (104) also being coupled to the input terminal of the tenth register (117), for using a smaller value between the length and the color value with the maximum brightness of each vertical line as the initial value of the tenth register (117);

the fourth multiplexer (122) outputting the second calculation value in the tenth register (117) to the fourth register (123) when the length of each vertical line is larger than or equal to the color value with the maximum brightness thereof, and outputting the first calculation value in the ninth register (118) to the fourth register (123) when the length of each vertical line is smaller than the color value with the maximum brightness thereof, and the fourth register (123) outputting the value therein based on a clock.

5. The waveform data display device according to claim 1, wherein the logic processing apparatus also comprises:
- a fixed-point number processing unit (2), for calculating the color values gradually changing along the length of the vertical line at different positions of each vertical line based on the information on the length and the color value with the maximum brightness of each vertical line, according to a fixed-point number algorithm;
- a fifth multiplexer (3) whose input terminal is coupled to the output terminal of the sloping line midpoint processing unit (1) and the output terminal of the fixed-point number processing unit (2) respectively; and
- a controller (5) for outputting a control signal to the control terminal of the fifth multiplexer (3) to control the switching of an output value of the fifth multiplexer (3) between a value output from the sloping line midpoint processing unit and a value output from the fixed-point number processing unit.

6. The waveform data display device according to claim 5, wherein the fixed-point number processing unit (2) comprises a reciprocal element (201), a third multiplier (203), a fifth register (202), a sixth register (204), a fourth subtracter (205) and a seventh register (206);

the reciprocal element (201) receiving the information on the length of each vertical line, and outputting a reciprocal of the length of each vertical line to the fifth register (202) whose input terminal is coupled to the input terminal of the third multiplier (203); the third multiplier (203) receiving the reciprocal of the length and the color value with the maximum brightness of each vertical line, and outputting a product of them to the sixth register (204) whose output terminal is coupled to the input terminal of the fourth subtracter (205); the input terminal of the seventh register (206) receiving the color value with the maximum brightness, and the output terminal of the seventh register (206) being coupled to the input terminal of the fourth subtracter (205) for outputting color values, and the output terminal of the fourth subtracter (205) being coupled to the seventh register(206) for updating the color values in the seventh register (206).

7. The waveform data display device according to claim 1, wherein the logic processing apparatus is implemented by FPGA or ASIC.

\* \* \* \* \*